US012274583B2

United States Patent
Arai et al.

(10) Patent No.: US 12,274,583 B2
(45) Date of Patent: Apr. 15, 2025

(54) ULTRASONIC THICKNESS MEASUREMENT DEVICE AND ULTRASONIC THICKNESS MEASUREMENT

(71) Applicant: SEIKO EPSON CORPORATION, Tokyo (JP)

(72) Inventors: Yoshio Arai, Shiojiri (JP); Kanechika Kiyose, Matsumoto (JP); Masahiro Onoda, Shimosuwa-machi (JP); Mio Sasaki, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 401 days.

(21) Appl. No.: 17/655,726

(22) Filed: Mar. 21, 2022

(65) Prior Publication Data

US 2022/0296217 A1  Sep. 22, 2022

(30) Foreign Application Priority Data

Mar. 22, 2021 (JP) ................................. 2021-047171

(51) Int. Cl.
*A61B 8/08* (2006.01)
*A61B 8/00* (2006.01)
(Continued)

(52) U.S. Cl.
CPC .............. *A61B 8/5215* (2013.01); *A61B 8/13* (2013.01); *G06T 7/62* (2017.01); *G06T 2207/10072* (2013.01); *G06T 2207/10132* (2013.01)

(58) Field of Classification Search
CPC ....... A61B 8/5215; A61B 8/13; A61B 8/0858; A61B 8/085; A61B 8/08; A61B 8/00;
(Continued)

(56) References Cited

U.S. PATENT DOCUMENTS

| 4,074,564 A  * | 2/1978 | Anderson .............. G01N 29/06 73/609 |
| 11,969,295 B2 * | 4/2024 | Taniguchi ........... G01S 7/52077 |

(Continued)

FOREIGN PATENT DOCUMENTS

| CN | 102639062 A * | 8/2012 | ........... A61B 5/4872 |
| JP | S61220634 A | 9/1986 | |

(Continued)

OTHER PUBLICATIONS

Office Action for JP Patent Application No. JP2021047171, issued on Jul. 30, 2024, 6 pages of Office Action.

(Continued)

*Primary Examiner* — Xuemei G Chen
(74) *Attorney, Agent, or Firm* — CHIP LAW GROUP

(57) ABSTRACT

An ultrasonic thickness measurement device includes ultrasonic probe including eight or less ultrasonic elements each including a transmission element and a receiving element, the transmission element and the receiving element being an ultrasonic elements, and a controller configured to determine a thickness of target body tissue from tomographic image data of a body of a subject acquired based on a received signal that is received by each of the receiving elements of each of the ultrasonic elements. The controller determines the thickness from the tomographic image data based on each of the received signals that is received by each of the ultrasonic elements.

12 Claims, 13 Drawing Sheets

(51) Int. Cl.
*A61B 8/13* (2006.01)
*G06T 7/62* (2017.01)

(58) Field of Classification Search
CPC ........... A61B 8/12; A61B 8/14; A61B 8/4227; A61B 8/5223; G06T 7/62; G06T 2207/10072; G06T 2207/10132; G06T 7/0012
See application file for complete search history.

(56) References Cited

U.S. PATENT DOCUMENTS

| | | | | |
|---|---|---|---|---|
| 2003/0018257 | A1* | 1/2003 | Hsu | A61B 8/0858 600/442 |
| 2005/0096541 | A1* | 5/2005 | Fukuda | G10K 11/345 600/447 |
| 2008/0089571 | A1* | 4/2008 | Kurita | A61B 8/08 382/131 |
| 2010/0036252 | A1* | 2/2010 | Chalana | G01S 7/52036 600/449 |
| 2010/0251822 | A1* | 10/2010 | Isobe | G01N 29/069 73/606 |
| 2011/0224551 | A1* | 9/2011 | Barnard | A61B 8/4281 600/459 |
| 2013/0081468 | A1* | 4/2013 | Falter | G01N 29/043 73/614 |
| 2013/0338506 | A1* | 12/2013 | Kim | G01S 7/52093 600/447 |
| 2014/0296713 | A1* | 10/2014 | Hyuga | A61B 8/461 600/449 |
| 2015/0049582 | A1* | 2/2015 | Miyachi | A61B 8/4483 367/7 |
| 2015/0359520 | A1* | 12/2015 | Shan | A61B 8/08 |
| 2017/0055950 | A1* | 3/2017 | Matsuda | A61B 8/4488 |
| 2017/0343655 | A1* | 11/2017 | Solek | G01S 15/8918 |
| 2019/0365350 | A1* | 12/2019 | Chiang | A61B 8/469 |
| 2020/0077985 | A1* | 3/2020 | Hope Simpson | G01S 15/8922 |
| 2021/0196227 | A1* | 7/2021 | Salinas | A61B 8/465 |

FOREIGN PATENT DOCUMENTS

| | | | | |
|---|---|---|---|---|
| JP | H06215878 A | * | 8/1994 | ............... F21S 10/00 |
| JP | 2003325517 A | | 11/2003 | |
| JP | 2005152605 A | | 6/2005 | |
| JP | 2012086002 A | | 5/2012 | |
| JP | 2015080570 A | | 4/2015 | |
| JP | 2016503706 A | | 2/2016 | |
| JP | 2018198791 A | | 12/2018 | |
| JP | 6709013 B1 | | 6/2020 | |
| WO | WO-2009026645 A1 | * | 3/2009 | ............... A61B 8/00 |
| WO | WO-2020036182 A1 | * | 2/2020 | ........... A61B 3/0025 |
| WO | WO-2020048875 A1 | * | 3/2020 | ............. A61B 8/085 |

OTHER PUBLICATIONS

Office Action for CN Patent Application No. 202210278719.6, issued on Dec. 31, 2024, 12 pages.

* cited by examiner

ULTRASONIC THICKNESS MEASUREMENT DEVICE AND ULTRASONIC THICKNESS MEASUREMENT

The present application is based on, and claims priority from JP Application Serial Number 2021-047171, filed Mar. 22, 2021, the disclosure of which is hereby incorporated by reference herein in its entirety.

BACKGROUND

1. Technical Field

The present disclosure relates to an ultrasonic thickness measurement device and an ultrasonic thickness measurement method for determining a thickness of target body tissue from an ultrasonic tomographic image of a body of a subject.

2. Related Art

A measurement device for measuring a muscle layer thickness and a fat layer thickness of a body by using ultrasonic waves has been known (JP-A-61-220634).

In JP-A-61-220634, a thickness of a muscle layer and a fat layer is estimated based on an A-mode image of an ultrasonic signal, but accuracy is insufficient. It is conceivable to increase the number of ultrasonic elements as a method for improving accuracy. However, in this case, the increase in the number of the ultrasonic elements leads to an increase in the amount of information processed by a processing unit that performs thickness estimation, and thus high processing capability is also required from a circuit system, thereby causing an increase in the size of the device. Further, there is a problem that a probe size also increases.

SUMMARY

In order to solve the problems described above, an ultrasonic thickness measurement device according to the present disclosure includes an ultrasonic probe including eight or less ultrasonic elements each including a transmission element and a receiving element, the transmission element and the receiving element being ultrasonic elements, and a controller configured to determine a thickness of target body tissue from tomographic image data of a body of a subject acquired based on a received signal that is received by each of the receiving elements of each of the ultrasonic elements, where the controller determines the thickness from the tomographic image data based on each of the received signals that is received by each of the ultrasonic elements.

Further, an ultrasonic thickness measurement method according to the present disclosure is an ultrasonic thickness measurement method for determining a thickness of target body tissue from tomographic image data of a body of a subject acquired by receiving, by receiving elements, a reflected wave of ultrasonic waves emitted to the body from eight or less ultrasonic elements including a transmission element and a receiving element, the transmission element and the receiving element being ultrasonic elements, and the method includes determining the thickness from the tomographic image data based on received signals that are received by the ultrasonic elements.

DESCRIPTION OF EXEMPLARY EMBODIMENTS

Figure 1:
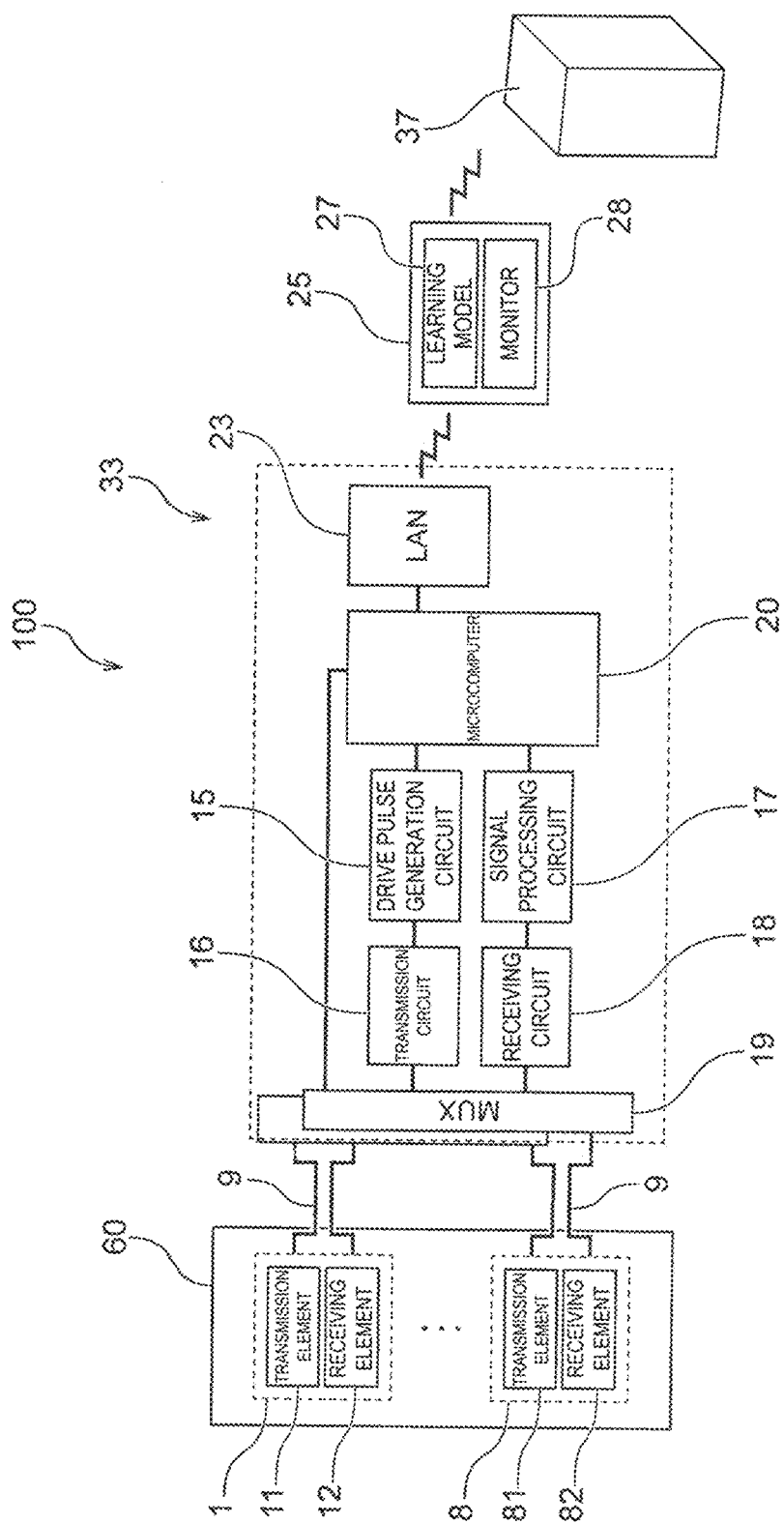
FIG. 1 is an overall schematic configuration diagram of an ultrasonic thickness measurement device in an exemplary embodiment 1 according to the present disclosure.

First, the present disclosure will be schematically described below.

In order to solve the problems described above, an ultrasonic thickness measurement device according to a first aspect of the present disclosure includes: an ultrasonic probe including eight or less ultrasonic elements including a transmission element and a receiving element, the transmission element and the receiving element being ultrasonic elements; and a controller configured to determine a thickness of target body tissue from tomographic image data of a body of a subject acquired based on a received signal that is received by each of the receiving elements of each of the ultrasonic elements, wherein the controller determines the thickness from the tomographic image data based on each of the received signals that is received by each of the ultrasonic elements.

Here, the "thickness" is not limited to a muscle layer thickness and a fat layer thickness of a body, and also includes a thickness for determining an organ having a layer structure, a thickness for determining an abnormal region, and the like.

According to this aspect, the controller determines the thickness from the tomographic image data based on each received signal that is received by the eight or less ultrasonic elements. The tomographic image data based on each received signal that is received by the eight or less ultrasonic elements is tomographic image data in a state where pieces of tomographic image data of eight or less lines along a depth direction from a skin surface are arranged.

In other words, the arrangement of pieces of the tomographic image data of the eight or less lines has a small amount of information processed for determining the thickness by the controller. In this way, high processing capability is not required from a circuit portion constituting the controller, and a size reduction of the device can be achieved. Further, the size of the ultrasonic probe can also be reduced.

In an ultrasonic thickness measurement device according to a second aspect of the present disclosure, the ultrasonic probe includes a base member configured to be mounted on a body, and the eight or less ultrasonic elements disposed at the base member.

According to this aspect, the number of the ultrasonic elements included in the ultrasonic probe is eight or less, and thus the size of the ultrasonic probe can be made smaller. The ultrasonic probe can be mounted on a body via the base member, and is thus convenient.

In an ultrasonic thickness measurement device according to a third aspect of the present disclosure in the first aspect or the second aspect, input tomographic image data used by the controller to determine the thickness is acquired by arranging, in association with an arrangement of each of the eight or less ultrasonic elements, B-mode images generated from A-mode images generated by processing each of the received signals that is received by the eight or less ultrasonic elements.

Each B-mode image generated from each A-mode image is an image in which brightness changes in the depth direction from skin, but brightness is fixed in a width direction of each line that is a direction intersecting the depth direction. In other words, the tomographic image in a state where the B-mode images of the eight or less lines are arranged is an image in which brightness appears to change in a block shape with respect to the depth direction for each line.

According to this aspect, input tomographic image data used by the controller to determine the thickness is tomographic image data in a state where the B-mode images of the eight or less lines are arranged, and is tomographic image data in which brightness changes in a block shape with respect to the depth direction for each line. In this way, the tomographic image data in which brightness changes in a block shape has a small amount of information processed by the controller to determine the thickness. Therefore, high processing capability is not required from the circuit portion constituting the controller, and a size reduction of the device can be achieved.

In an ultrasonic thickness measurement device according to a fourth aspect of the present disclosure in any one of the first aspect to the third aspect, the controller is configured to access a learning model including a parameter for acquiring, from input tomographic image data, attribute information corresponding to the thickness of the target body tissue, and performs processing of determining attribute information corresponding to the thickness by using the learning model with, as input image data, the tomographic image data of the body of the subject, and determines the thickness from the determined attribute information.

According to this aspect, the controller performs processing of determining attribute information corresponding to the thickness by using the learning model with, as input image data, the tomographic image data of the body of the subject, and determines the thickness from the determined attribute information. In this way, the thickness of the target body tissue can be automatically determined with high accuracy.

In an ultrasonic thickness measurement device according to a fifth aspect of the present disclosure in the fourth aspect, with, as one set of data, tomographic image data based on each of the received signals that is received from the target body tissue by the eight or less ultrasonic elements, and supervised image data corresponding to the tomographic image data and in a state where the thickness is determined, the learning model performs learning on a plurality of sets of data to set a parameter for acquiring, from input tomographic image data, attribute information corresponding to the thickness of the target body tissue.

According to this aspect, a parameter of the learning model used for acquiring, from the input tomographic image data, attribute information corresponding to the thickness of the target body tissue is set by learning the tomographic image data in a state where B-mode images of the eight or less lines are arranged similarly to the input tomographic image data. Therefore, the setting of the parameter of the learning model can be performed by using the tomographic image data having a small amount of information as described above.

In an ultrasonic thickness measurement device according to a sixth aspect of the present disclosure in the fourth aspect or the fifth aspect, the controller is coupled to the learning model via a communication unit in a wireless or wired manner, and the learning model is configured to have the parameter updated by new tomographic image data and supervised image data corresponding to the new tomographic image data.

According to this aspect, the learning model can have the parameter updated by new tomographic image data and supervised image data corresponding to the new tomographic image data. In this way, attribute information corresponding to a thickness of target body tissue can be accurately acquired from input tomographic image data.

An ultrasonic thickness measurement method according to a seventh aspect of the present disclosure is an ultrasonic thickness measurement method for determining a thickness of target body tissue from tomographic image data of a body of a subject acquired by receiving, by receiving elements, a reflected wave of ultrasonic waves emitted to the body from eight or less ultrasonic elements each including a transmission element and a receiving element, the transmission element and the receiving element being ultrasonic elements, and the method includes determining the thickness from the tomographic image data based on received signals that are received by the eight or less ultrasonic elements.

According to this aspect, an effect similar to that in the first aspect can be obtained.

An ultrasonic thickness measurement method according to an eighth aspect of the present disclosure in the seventh aspect includes: accessing a learning model including a parameter for acquiring, from input tomographic image data, attribute information corresponding to the thickness of the target body tissue; and performing processing of determining attribute information corresponding to the thickness by using the learning model with, as input image data, the tomographic image data of the body of the subject, and determining the thickness from the determined attribute information.

According to this aspect, an effect similar to that in the fourth aspect can be obtained.

Exemplary Embodiment 1

An ultrasonic thickness measurement device in an exemplary embodiment 1 according to the present disclosure will be described below in detail with reference to FIGS. 1 to 7.

Figure 3:
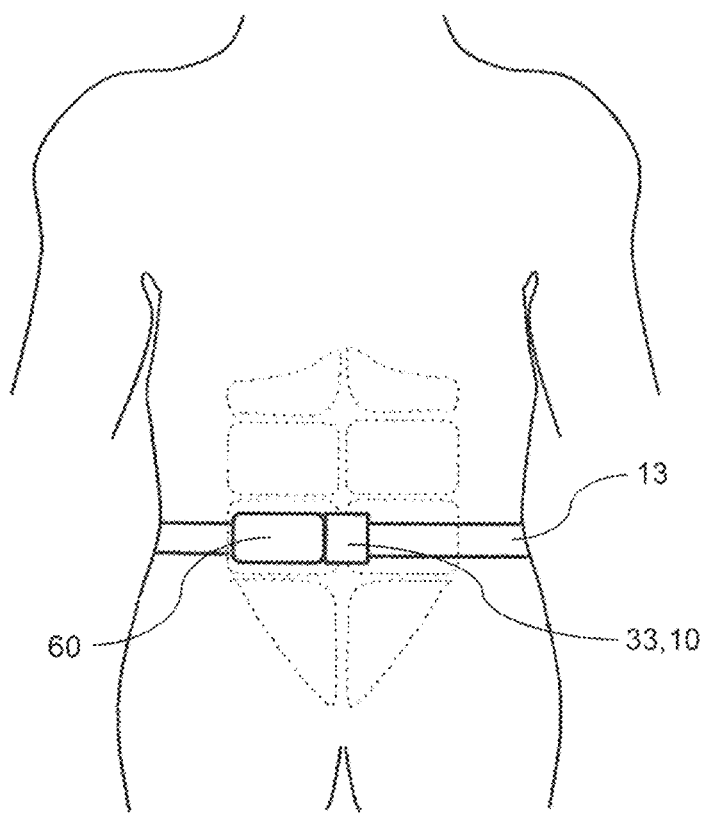
FIG. 3 is a front view of a state where the ultrasonic probe in the exemplary embodiment 1 is mounted on a body.

As illustrated in FIG. 1, an ultrasonic thickness measurement device 100 includes an ultrasonic probe 60 including an ultrasonic element that emits and receives ultrasonic waves, and a controller 33 that performs control of a function of the ultrasonic probe 60 and performs signal processing. The controller 33 is accommodated in a housing portion 10 (FIG. 3).

Ultrasonic Probe

Figure 2:
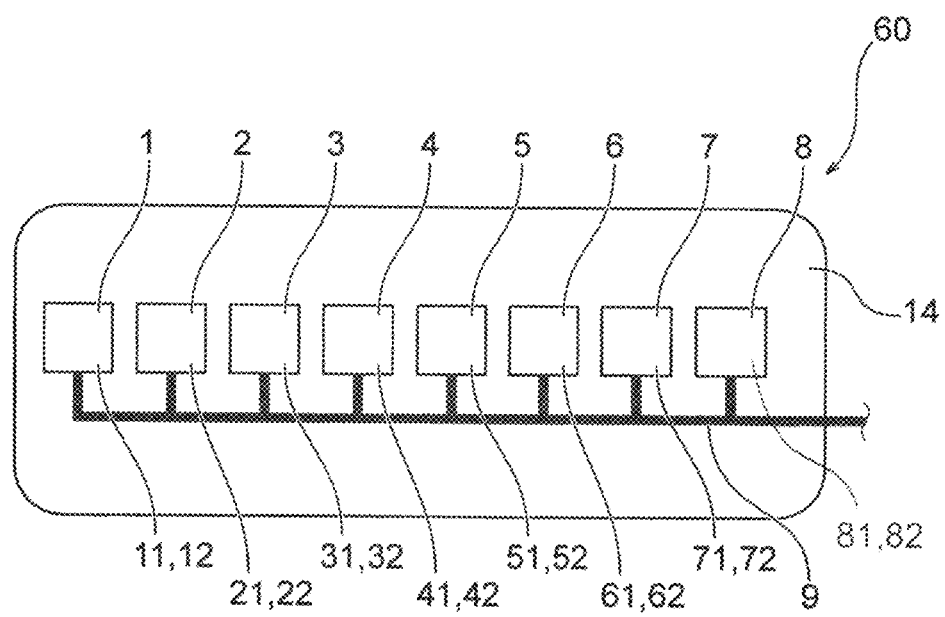
FIG. 2 is a schematic front view of an ultrasonic probe in the exemplary embodiment 1.

As illustrated in FIGS. 1 and 2, in the present exemplary embodiment, the ultrasonic probe 60 includes eight ultrasonic elements 1, 2, 3, 4, 5, 6, 7, and 8. In FIG. 1, the six ultrasonic elements 2, 3, 4, 5, 6, and 7 other than the ultrasonic element 1 and the ultrasonic element 8 are not illustrated. As illustrated in FIG. 1, the ultrasonic element 1 includes an ultrasonic transmission element 11 and an ultrasonic receiving element 12, and the ultrasonic element 8 includes an ultrasonic transmission element 81 and an ultrasonic receiving element 82. As illustrated in FIG. 2, the other six ultrasonic element 2, ultrasonic element 3, ultrasonic element 4, ultrasonic element 5, ultrasonic element 6, and ultrasonic element 7 similarly include ultrasonic transmission elements 21, 31, 41, 51, 61, and 71 and ultrasonic receiving elements 22, 32, 42, 52, 62, and 72, respectively.

Here, "including an ultrasonic transmission element and an ultrasonic receiving element" is described in terms of a function, and one ultrasonic element functions as a "transmission element" and functions as a "receiving element" in terms of structure. In FIG. 2, reference sign 9 indicates wiring.

As illustrated in FIG. 2, the ultrasonic probe 60 includes a base member 14 (FIG. 2) that has a flat plate shape, and can be mounted on a body, and the eight ultrasonic elements 1, 2, 3, 4, 5, 6, 7, and 8 disposed at regular intervals in a row on the base member 14.

As illustrated in FIG. 3, in the present exemplary embodiment, the ultrasonic probe 60 of the ultrasonic thickness measurement device 100 and the housing portion 10 that accommodates the controller 33 are attached to a belt 13. In other words, a portion of the ultrasonic probe 60 and the controller 33 is configured to be wrapped around an abdomen of the body and be fixed by the belt 13. Specifically, as illustrated in FIG. 3, the belt 13 is mounted on a target portion of the body, and thus a thickness of a target muscle layer and the like can be measured.

Controller

The controller 33 determines a thickness of target body tissue from tomographic image data (FIG. 5) of a body of a subject acquired based on received signals that are sequentially received by the receiving elements 12, 22, 32, 42, 52, 62, 72, and 82 of the ultrasonic elements 1, 2, 3, 4, 5, 6, 7, and 8, respectively.

In other words, the controller 33 determines the thickness from the data (FIGS. 4 and 5) of a tomographic image 30, which will be described below, based on each of the received signals that are sequentially received by the eight ultrasonic elements 1, 2, 3, 4, 5, 6, 7, and 8.

As illustrated in FIG. 1, the controller 33 includes a drive pulse generation circuit 15, a transmission circuit 16, a signal processing circuit 17, a receiving circuit 18, a multiplexer 19, a microcomputer 20, and a communication unit 23. The controller 33 is configured to be able to access a tablet 25 via the communication unit 23. The tablet 25 is equipped with a learning model 27 described below.

Upon transmission of ultrasonic waves, a pattern of a predetermined drive frequency and wavenumber is generated in the drive pulse generation circuit 15, a transmission waveform of a predetermined drive voltage is output from the transmission circuit 16, and ultrasonic waves are transmitted from each of the transmission elements 11, 21, 31, 41, 51, 61, 71, and 81 of the ultrasonic elements 1, 2, 3, 4, 5, 6, 7, and 8, respectively.

Figure 4:
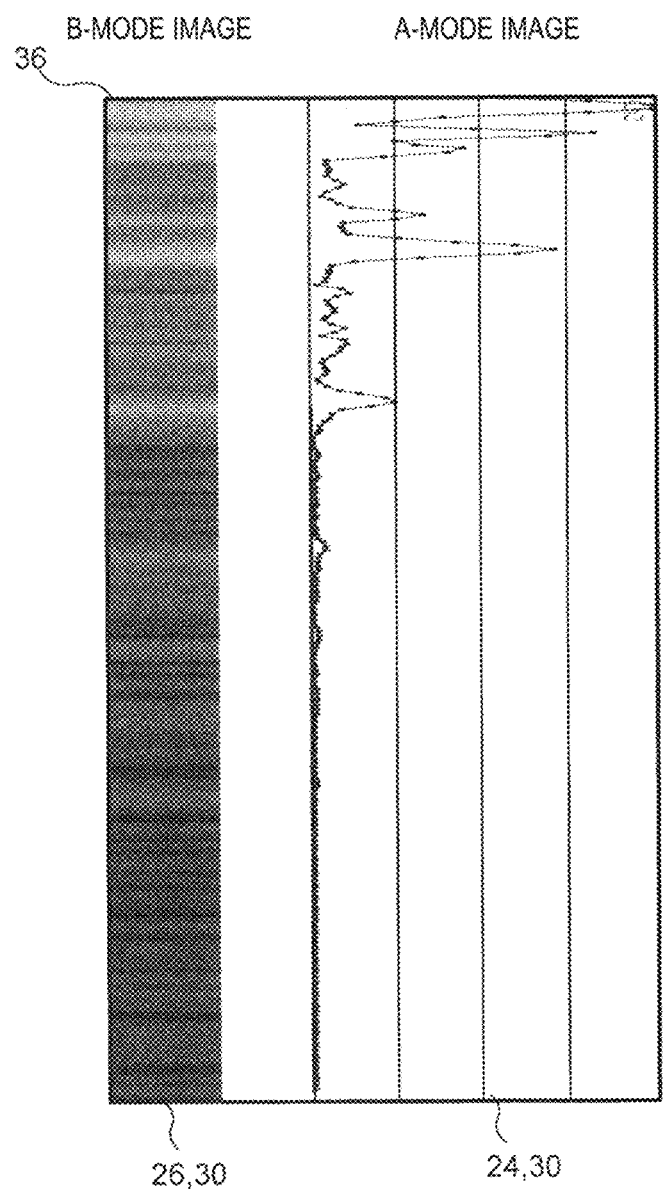
FIG. 4 is a diagram of an A-mode image acquired by one ultrasonic element in the exemplary embodiment 1 and a corresponding B-mode image of one line.

Upon reception of ultrasonic waves, a received signal by each of the receiving elements 12, 22, 32, 42, 52, 62, 72, and 82 of the ultrasonic elements 1, 2, 3, 4, 5, 6, 7, and 8, respectively, is amplified by the receiving circuit 18, and is subjected to envelope processing and LOG compression processing in the signal processing circuit 17 to generate an A-mode image 24 that is the tomographic image 30 of each of the eight ultrasonic elements 1, 2, 3, 4, 5, 6, 7, and 8. FIG. 4 illustrates the A-mode image 24 generated from a received signal of one ultrasonic element.

Control of each operation of each of the circuits 15, 16, 17, and 18 is performed via the microcomputer 20. Furthermore, the microcomputer 20 is configured to sequentially switch, in the multiplexer 19, each transmission-reception operation of transmission and reception of each of the eight ultrasonic elements 1, 2, 3, 4, 5, 6, 7, and 8. In other words, the eight ultrasonic elements 1, 2, 3, 4, 5, 6, 7, and 8 are configured to sequentially receive the received signals.

In the present exemplary embodiment, by control of the microcomputer 20, data of the eight A-mode images 24 of the eight ultrasonic elements 1, 2, 3, 4, 5, 6, 7, and 8 is sent to the tablet 25 equipped with the learning model 27 via the communication unit 23. The communication unit 23 is formed of a wireless LAN circuit in the present exemplary embodiment, but may be formed in a wired manner.

The tablet 25 includes a GPU, and generates data of eight B-mode images 26 from the sent data of the eight A-mode images 24. FIG. 4 illustrates one B-mode image 26 corresponding to one A-mode image 24.

The input data of the tomographic image 30 used by the controller 33 to determine the thickness is acquired by arranging, in association with an arrangement of each of the eight ultrasonic elements 1, 2, 3, 4, 5, 6, 7, and 8, each of the B-mode images 26 generated from each of the A-mode images 24 generated by processing each of the received signals that are sequentially received by the eight ultrasonic elements 1, 2, 3, 4, 5, 6, 7, and 8.

Figure 5A:
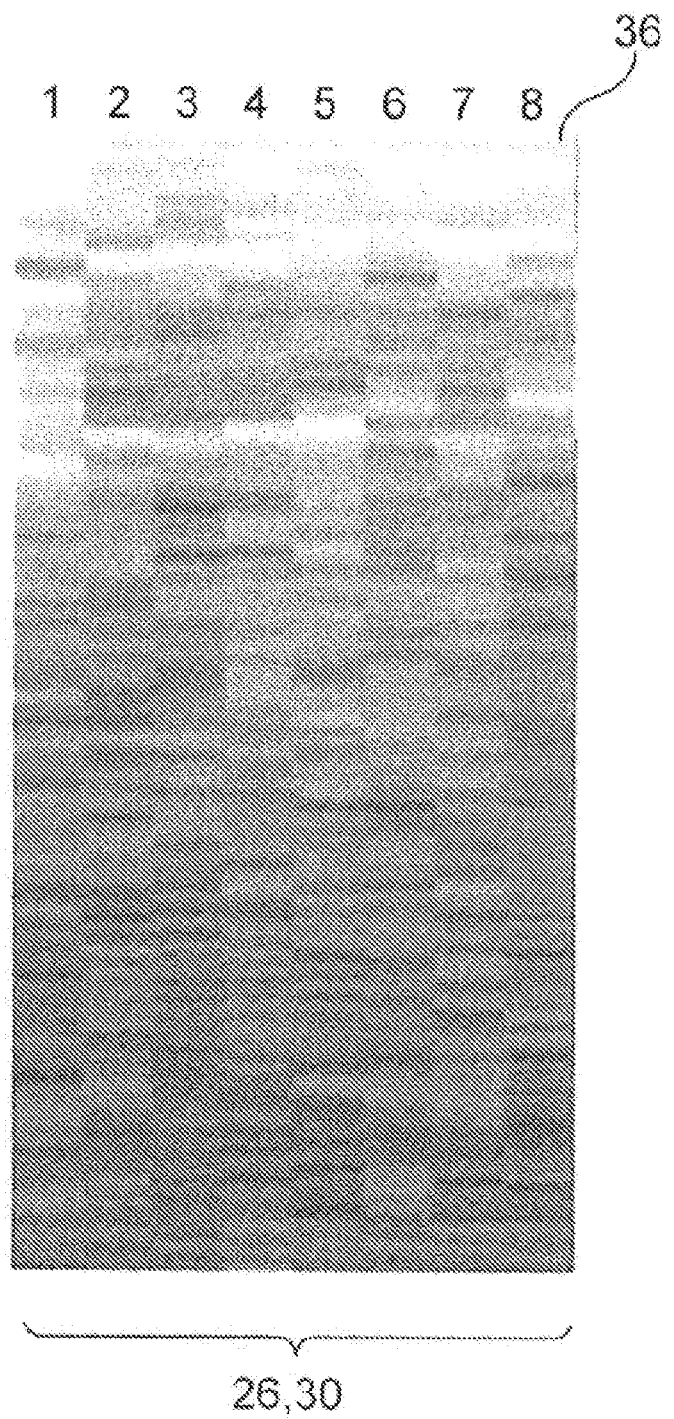
FIG. 5A is a diagram of input image data formed of B-mode images of eight lines input for determining a target thickness to a controller in the exemplary embodiment 1.

FIG. 5A illustrates an arrangement of the eight B-mode images 26 in association with an arrangement of the eight ultrasonic elements 1, 2, 3, 4, 5, 6, 7, and 8. In other words, FIG. 5A illustrates data of the B-mode images 26 of eight lines with pieces of tomographic image data of eight lines being arranged along a depth direction (downward in the diagram) from a skin surface 36. The data of the B-mode images 26 of the eight lines is input image data used for determining the thickness.

Figure 5B:
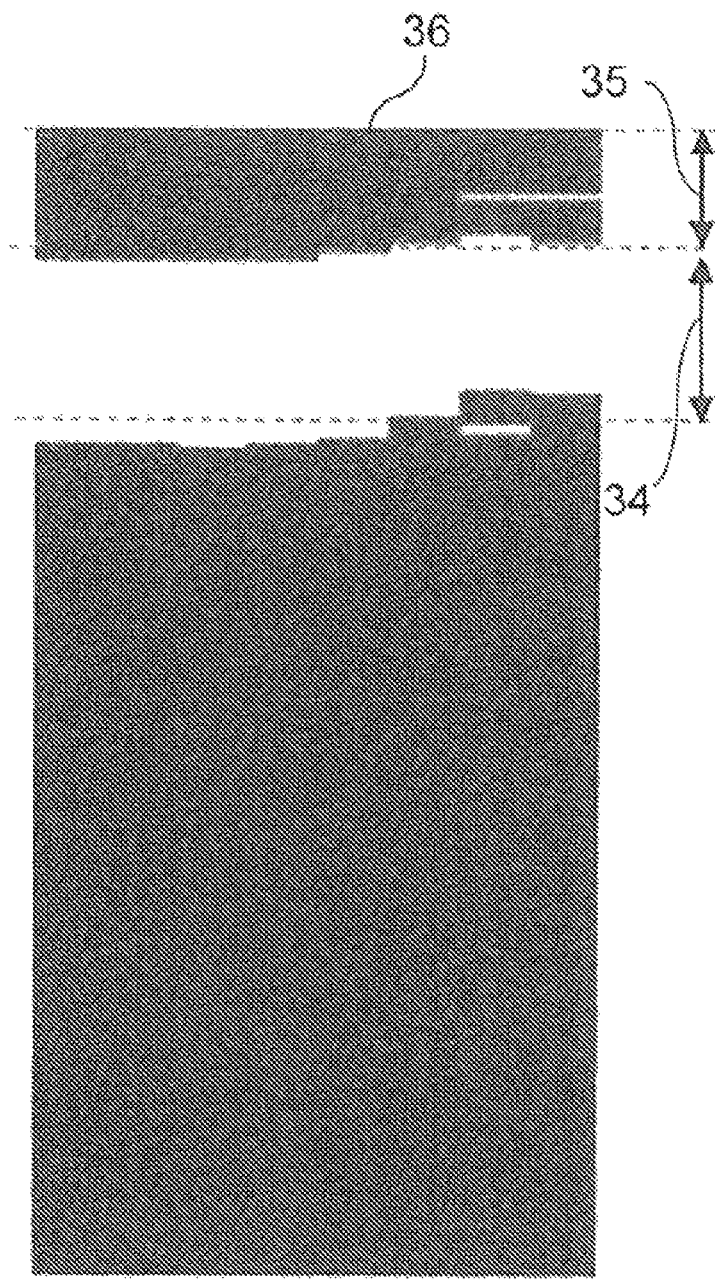
FIG. 5B is a diagram of output image data in which the target thickness output from the controller is estimated.

As described above, the controller 33 can access the learning model 27 having a parameter for acquiring, from input data of the tomographic image 30, attribute information corresponding to a thickness of the target body tissue. The controller 33 is configured to perform processing of determining attribute information corresponding to the thickness by using the learning model 27 mounted on the tablet 25 with, as input image data, data of the B-mode images 26 of the eight lines (FIG. 5A) being data of the tomographic image 30 of a body of a subject, and to determine the thickness from the determined attribute information. The determined thickness is displayed as output image data on a monitor 28 of the tablet 25 as described below (FIG. 5B).

Note that the learning model 27 may be mounted on a computer, such as a notebook computer, instead of the tablet 25.

Here, examples of the "attribute information corresponding to a thickness" include, for example, information about a position of a boundary portion between a fat layer and a muscle layer acquired by using emitted ultrasonic waves that are often reflected on the boundary portion and are rarely reflected in the muscle layer and in the fat layer. When one surface of the muscle layer is in contact with the fat layer, and the other surface is in contact with another fat layer, positions of "one boundary portion" corresponding to the one surface of the muscle layer and "another boundary portion" corresponding to the other surface of the muscle layer can be determined by ultrasonic waves. A distance between the "one boundary portion" and the "other boundary portion" is a determined thickness of the muscle layer.

Alternatively, when a thickness of subcutaneous fat is determined, a position of a boundary portion between the subcutaneous fat and a muscle layer located deeper than the subcutaneous fat is determined as "attribute information" by ultrasonic waves, and thus a distance between the determined boundary portion and a skin surface is a thickness of the subcutaneous fat.

FIG. 5B illustrates output image data displayed on the monitor 28 of the tablet 25. In the present exemplary embodiment, image data in which a muscle layer thickness 34 and a subcutaneous fat thickness 35 are clear with the muscle layer in white is displayed.

Parameter of Learning Model

In the present exemplary embodiment, the learning model 27 is constructed as follows.

Figure 6A:
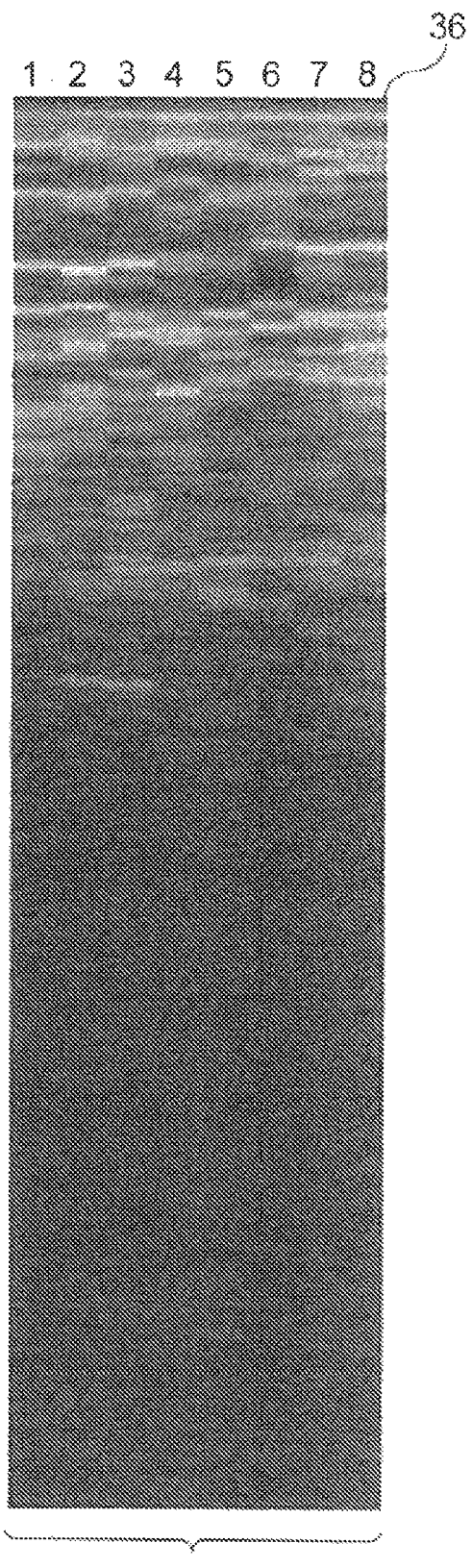
FIG. 6A is a diagram of input image data formed of the B-mode images of the eight lines in the exemplary embodiment 1.
Figure 6B:
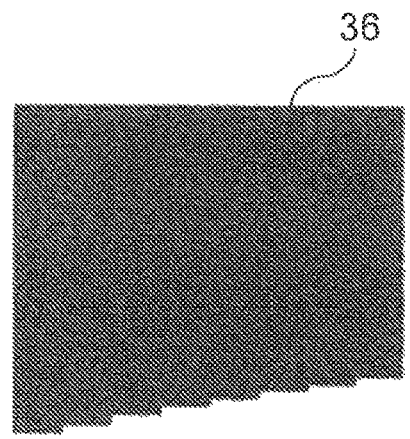
FIG. 6B is a diagram of supervised data corresponding to the input image data.
Figure 6B:
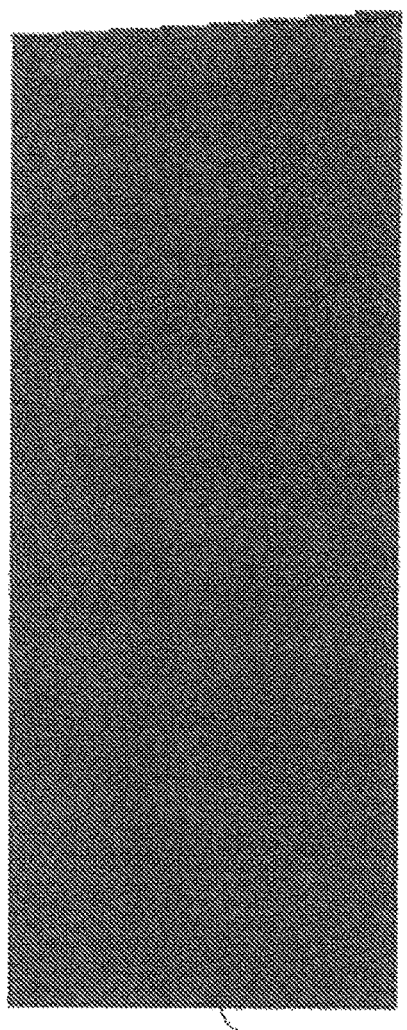

As illustrated in FIG. 6, with, as one set of data, the B-mode images 26 (FIG. 6A) of the eight lines being data of the tomographic image 30 based on each of the received signals that are sequentially received from body tissue in a region specified by the eight ultrasonic elements 1, 2, 3, 4, 5, 6, 7, and 8, and supervised image data 50 (FIG. 6B) corresponding to the B-mode images 26 of the eight lines and in a state where the thickness is determined, a plurality of the sets, for example, 100 or more of the sets are prepared. Then, machine learning is performed on the plurality of prepared sets of data to set a parameter for acquiring, from input image data, attribute information corresponding to the thickness of the target body tissue.

Examples of a method for generating a learning model include a convolutional processing method in U-Net for a purpose of dividing a medical image into regions. Specifically, normal convolutional processing in a neural network of machine learning and, furthermore, pooling processing are performed on the B-mode images 26 of the eight lines in FIG. 6A. Output image data acquired by the processing is compared with the supervised image data 50 in FIG. 6B, and an operation is performed so as to reduce an error, i.e., an operation is performed by using a cross entropy error function and a gradient descent method to set a parameter. The setting is performed on 100 or more of the sets to optimize the parameter.

In the present exemplary embodiment, as illustrated in FIG. 1, the tablet 25 is coupled to a learning model generation center 37 via a communication line. The setting of the parameter is performed in the learning model generation center 37. Every time estimation accuracy is improved, a result thereof is transmitted to the tablet 25 to update the learning model 27.

The learning model 27 may also be constructed as follows.

Figure 7A:
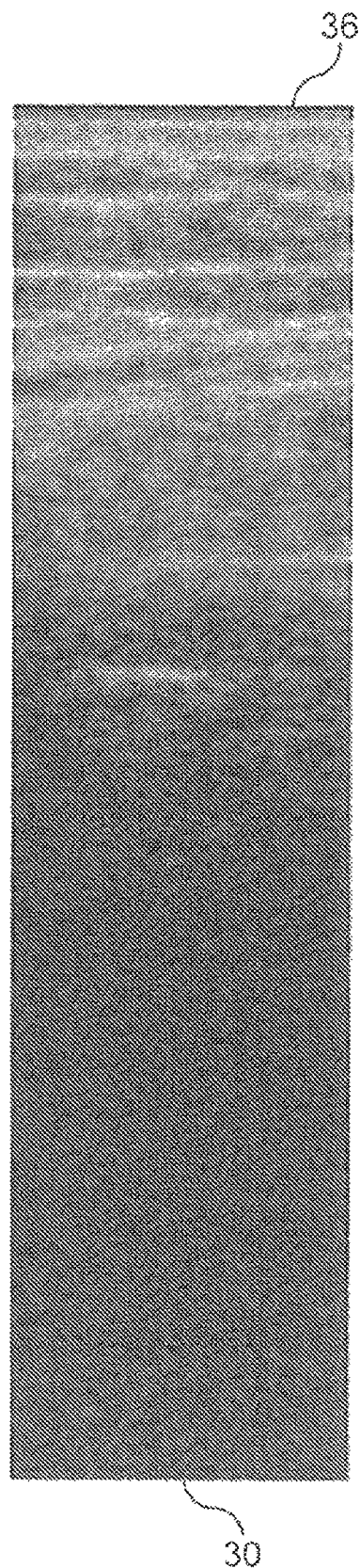
FIG. 7A is a diagram of input image data formed of a B-mode image acquired by an ultrasonic probe including 64 or more ultrasonic elements.
Figure 7B:
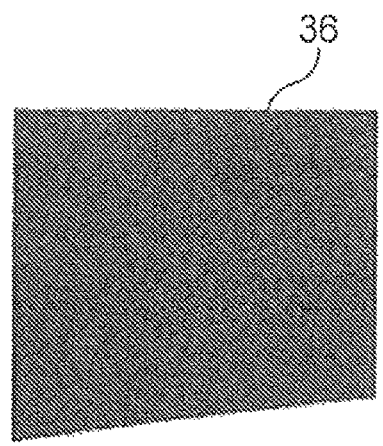
FIG. 7B is a diagram of supervised data corresponding to the input image data.
Figure 7B:
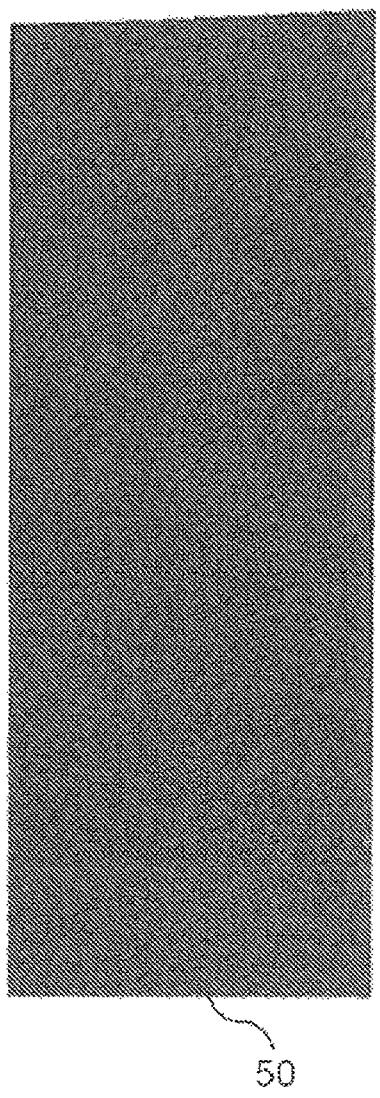

FIG. 7A is a diagram of input image data formed of the tomographic image 30 of the B-mode image acquired, by using an ultrasonic probe including 64 or more ultrasonic elements, from 64 or more received signals that are received by all of the ultrasonic elements. FIG. 7B is a diagram of the supervised image data 50 corresponding to the input image data.

With, as one set of data, tomographic image data and supervised data having eight lines cut at a sensor arrangement interval from the data of the tomographic image 30 in FIG. 7A and the supervised image data 50 in FIG. 7B, respectively, for example, 100 or more of the sets may be prepared, and machine learning similar to that described above may be performed to set a parameter for acquiring, from the input image data, attribute information corresponding to the thickness of the target body tissue. The B-mode image by the 64 or more ultrasonic elements has an advantage that it is easy to determine a muscle layer and to create the supervised data.

In the present exemplary embodiment, the controller 33 is coupled to the learning model 27 via the communication unit 23 in a wireless manner, and the learning model 27 can have the parameter updated by new data of the tomographic image 30 corresponding to FIG. 6A and the supervised image data 50 corresponding to FIG. 6B and corresponding to the new data of the tomographic image 30.

In other words, new data of the tomographic image 30 of tissue in a specific region of a body is first acquired by ultrasonic waves to determine a thickness of the target body tissue. In addition, the new data of the tomographic image 30 is sent from the tablet 25 to the learning model generation center 37 to perform a parameter update operation of the learning model 27 from a set of the supervised image data 50 corresponding to the image. When estimation accuracy is improved, a result thereof is transmitted to the tablet 25 to update the parameter of the learning model 27.

DESCRIPTION ON ACTIONS OF EXEMPLARY EMBODIMENT 1

Next, a step of determining a thickness of target body tissue by the ultrasonic thickness measurement device 100 in the exemplary embodiment 1 is performed.

First, the portion of the ultrasonic probe 60 and the controller 33 of the ultrasonic thickness measurement device 100 in the present exemplary embodiment is wrapped around an abdomen of a body of a subject and is fixed by the belt 13 as illustrated in FIG. 3. Then, ultrasonic waves are sequentially transmitted and received by the eight ultrasonic elements 1, 2, 3, 4, 5, 6, 7, and 8 to generate eight A-mode images 24 based on eight received signals, and further generate eight B-mode images 26 from the eight A-mode images 24 by the tablet 25, i.e., generate data of the B-mode images 26 of the eight lines (FIG. 5A).

Next, with the data of the B-mode images 26 of the eight lines (FIG. 5A) as input image data, processing of determining attribute information corresponding to the thickness is performed by using the learning model 27, and the thickness is determined from the determined attribute information (FIG. 5B) and is displayed on the monitor 28.

Note that the information related to the thickness displayed on the monitor 28 is not limited to the form illustrated in FIG. 5B, and may be in the form of a numerical value and a comparable graph, for example.

DESCRIPTION ON EFFECTS OF EXEMPLARY EMBODIMENT 1

(1) According to the present exemplary embodiment, the controller 33 determines a thickness of target body tissue from a tomographic image based on each of the received signals that are sequentially received by the eight ultrasonic elements 1, 2, 3, 4, 5, 6, 7, and 8. Tomographic image data based on each of the received signals that are sequentially received by the eight ultrasonic elements 1, 2, 3, 4, 5, 6, 7, and 8 is tomographic image data (FIG. 5A) in which pieces of data of the tomographic images 30 of eight lines along the depth direction from the skin surface 36 are arranged.

In other words, the arrangement (FIG. 5A) of the data of each of the tomographic images 30 of the eight lines has a small amount of information processed for determining the thickness by the controller 33. In this way, high processing capability is not required from a circuit portion constituting the controller 33, and a size reduction of the device 100 can be achieved. Further, the size of the ultrasonic probe 60 can also be reduced.

(2) Further, in the present exemplary embodiment, the number of the ultrasonic elements included in the ultrasonic probe 60 is eight, and thus the size of the ultrasonic probe 60 can be made smaller than a known ultrasonic probe. The ultrasonic probe 60 can be mounted on a body via the base member 14, and is thus convenient. (3) As illustrated in FIG. 4, the B-mode image 26 generated from the A-mode image 24 is an image in which brightness changes on one line in the depth direction from the skin surface 36, but brightness is fixed in a width direction of the line that is a direction intersecting the depth direction. In other words, brightness changes in a block shape with respect to the depth direction on the one line. As illustrated in FIG. 5A, the tomographic image 30 in a state where the B-mode images of the eight lines are arranged is an image in which brightness appears to change in a block shape with respect to the depth direction for each line.

According to the present exemplary embodiment, the input data of the tomographic image 30 used by the controller 33 to determine the thickness is tomographic image data (FIG. 5A) in a state where the B-mode images 26 of the eight lines are arranged, and is tomographic image data in which brightness changes in a block shape with respect to the depth direction for each line. In this way, the data of the tomographic image 30 in which brightness changes in a block shape has a small amount of information processed by the controller 33 to determine the thickness. Therefore, high processing capability is not required from the circuit portion constituting the controller 33, and a size reduction of the device 100 can be achieved.

(4) Further, in the present exemplary embodiment, the controller 33 performs processing of determining attribute information corresponding to the thickness by using the learning model 27 with, as input image data, data of the tomographic image 30 of a body of a subject, and determines the thickness from the determined attribute information. In this way, the thickness of the target body tissue can be automatically determined with high accuracy.

(5) Further, in the present exemplary embodiment, a parameter of the learning model 27 used for acquiring, from the input data of the tomographic image 30, attribute information corresponding to the thickness of the target body tissue is set by learning the tomographic image data (FIG. 6A) in a state where B-mode images of eight lines are arranged similarly to the input data of the tomographic image 30. Therefore, the setting of the parameter of the learning model 27 can be performed by using the data of the tomographic image 30 having a small amount of information as described above.

(6) Further, in the present exemplary embodiment, the learning model 27 can have the parameter updated by new data of the tomographic image 30 (FIG. 6A) and supervised image data (FIG. 6B) corresponding to the new data of the tomographic image 30. In this way, attribute information corresponding to a thickness of target body tissue can be accurately acquired from input data of the tomographic image 30.

Exemplary Embodiment 2

Next, an ultrasonic thickness measurement device 100 according to an exemplary embodiment 2 of the present disclosure will be described with reference to FIGS. 8 and 9.

Figure 8:
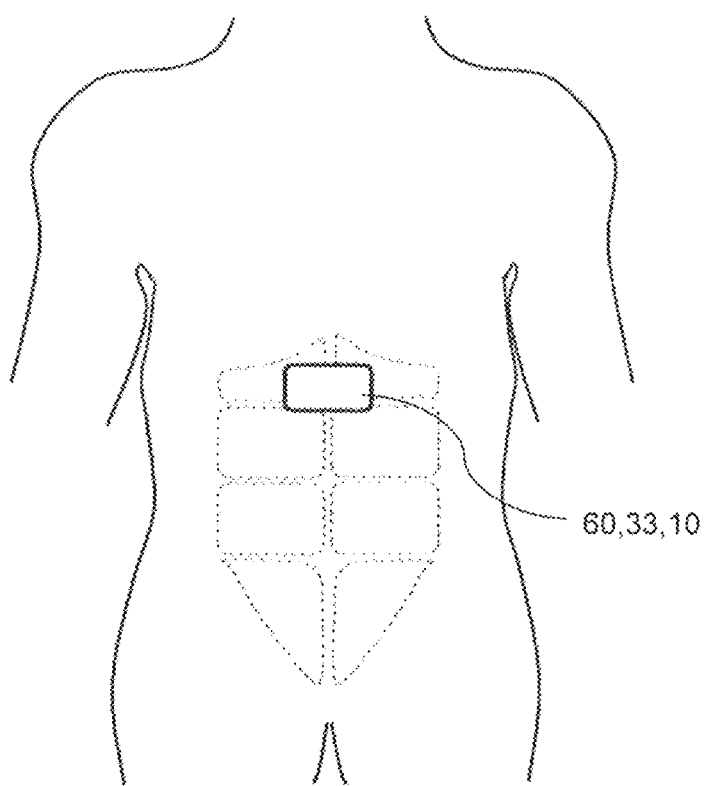
FIG. 8 is a schematic front view of a state where an ultrasonic probe is mounted in a position of a body different from that in FIG. 3.
Figure 9:
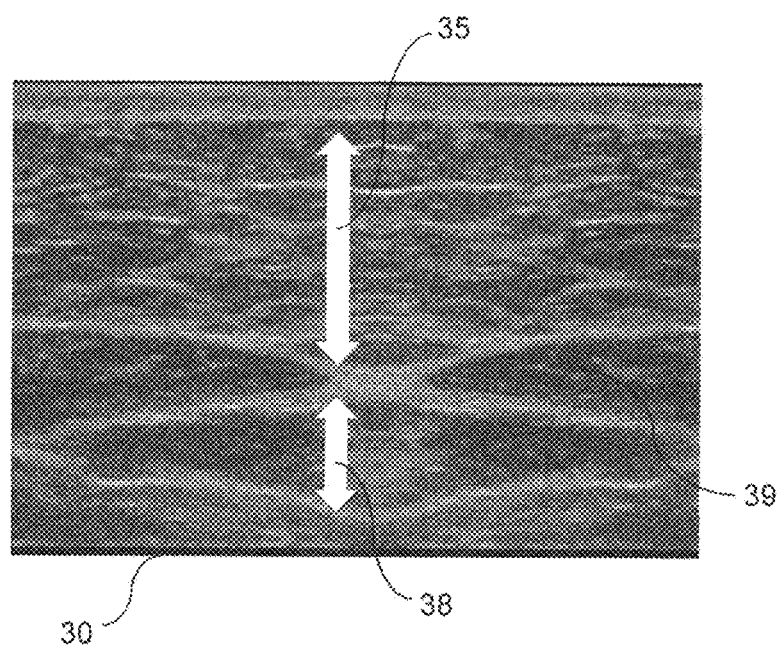
FIG. 9 is a diagram of a B-mode image acquired by the ultrasonic probe mounted in the position in FIG. 8.

The ultrasonic thickness measurement device 100 in the present exemplary embodiment is used for determining a visceral fat thickness, and a portion of an ultrasonic probe 60 and a controller 33 is mounted and used on a pit of a stomach of a body as illustrated in FIG. 8. A belt 13 is not illustrated in FIG. 8. FIG. 9 is a tomographic image 30 of the pit of the stomach of the body. The tomographic image 30 in FIG. 9 is a diagram of a B-mode image acquired, by using an ultrasonic probe including 64 or more ultrasonic elements, from 64 or more received signals that are received by all of the ultrasonic elements. The pit of the stomach of the body does not have a rectus abdominis muscle 39, and an image for subcutaneous fat 35 and an image for visceral fat 38 can be acquired.

Therefore, by measuring the pit of the stomach by using the ultrasonic thickness measurement device 100 in the present exemplary embodiment, similarly to the exemplary embodiment 1, a learning model 27 including a parameter for determining a visceral fat thickness can be created similarly to that described above, and a visceral fat thickness of a subject can be determined by using the learning model 27 similarly to that described above.

Exemplary Embodiment 3

Next, an exemplary embodiment 3 of the present disclosure will be described with reference to FIG. 10.

Figure 10:
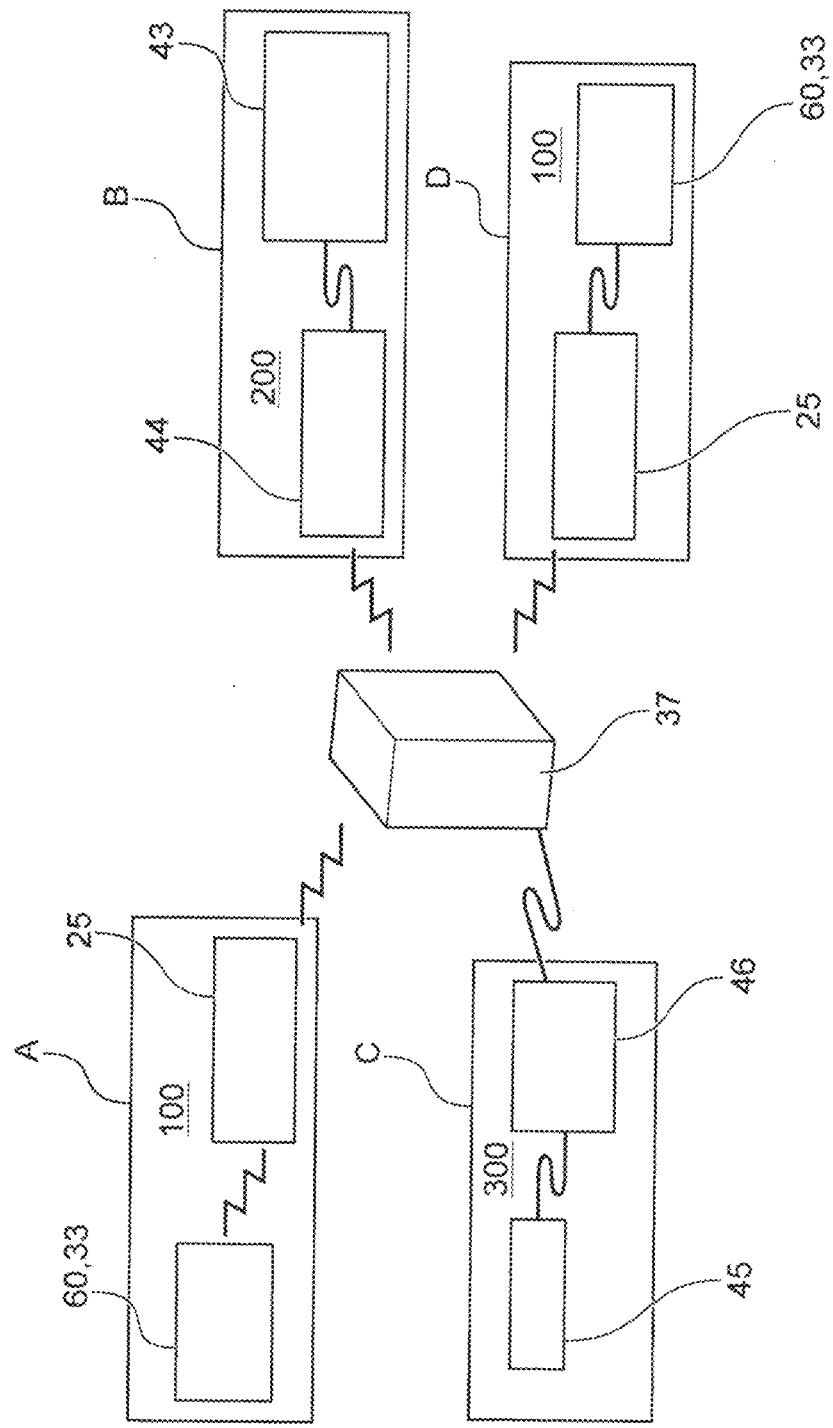
FIG. 10 is a system diagram of updating of a learning model.

FIG. 10 illustrates a state where four ultrasonic thickness measurement devices are used individually by a user A, a user B, a user C, and a user D and are coupled in a wireless or wired manner to a learning model generation center 37 as the center.

The user A and the user D are both individual users, and use an ultrasonic thickness measurement device 100 in the present exemplary embodiment. The user B is a training gym, and uses an ultrasonic thickness measurement device 200 for visually recognizing an abdominal muscle and a fat thickness by using a notebook computer 44 including a learning model with a portable echo probe 43 or the like. The user C is a health care facility, and uses an ultrasonic thickness measurement device 300 formed of an ultrasonic diagnostic device coupled to a normal ultrasonic probe 45.

Data of a tomographic image 30 acquired through each use from the user A, the user B, the user C, and the user D is sent to the learning model generation center 37. The learning model generation center 37 specifies body tissue, i.e., a muscle layer and a fat layer being a target of data of each of the collected tomographic images 30 to create supervised image data (FIGS. 6B and 7B), and generates a learning model 27 and a parameter for the specified body tissue. This is performed on the data of each of the sent tomographic images 30 to improve the accuracy of the learning model 27 and the parameter. It can be said that the accuracy of the learning model 27 improves with an increase in the data of the collected tomographic images 30. Every time the parameter of the learning model 27 is updated to improve the accuracy, a latest parameter is sent from the learning model generation center 37 to the tablet 25 and a notebook computer equipped with the learning model 27 to update the learning mode 27.

Other Exemplary Embodiments

The ultrasonic thickness measurement device 100 according to the exemplary embodiments of the present disclosure is based on the configuration described above. However, as a matter of course, modifications, omission, and the like may be made to a partial configuration without departing from the gist of the disclosure of the present application.

(1) In the exemplary embodiments described above, a structure in which the ultrasonic probe 60 includes the eight ultrasonic elements 1, 2, 3, 4, 5, 6, 7, and 8 is described, but the present disclosure is not limited to the eight ultrasonic elements. Four ultrasonic elements, which are less than eight, may be used, and tomographic image data of four lines may be arranged. Further, the number of the ultrasonic elements may be 16 or 32, which is more than eight, and the number of received signals may be equal to or less than eight by setting eight or less ultrasonic elements among the ultrasonic elements to receive the received signal.

(2) In the exemplary embodiments described above, the portion of the ultrasonic probe 60 and the controller 33 is configured to be wrapped around an abdomen of a body and be fixed by the belt 13, but, as a matter of course, the present disclosure is not limited to this. The ultrasonic probe 60 may be an ultrasonic echo probe being generally used.

(3) In the exemplary embodiments described above, a structure in which the controller 33 and the learning model 27 are separated is described, but the present disclosure may have a configuration in which the learning model 27 and the communication unit 23 are provided in the controller 33.

What is claimed is:

1. An ultrasonic thickness measurement device comprising:
    an ultrasonic probe including eight or less ultrasonic elements each including a transmission element and a receiving element, the transmission element and the receiving element being the ultrasonic elements; and
    a controller configured to determine a thickness of a target body tissue from tomographic image data of a body of a subject acquired based on received signals that is received by receiving elements of each of the ultrasonic elements, wherein
        the tomographic image data is image data in which data of each of tomographic images of eight or less lines corresponding to the eight or less ultrasonic elements is arranged, along a depth direction from a skin surface of the body of the subject,
        the thickness is determined from the tomographic image data that is acquired by arranging, in association with an arrangement of each of the eight or less ultrasonic elements, B-mode images generated from A-mode images, and
        the A-mode images are generated by processing each of the received signals that is sequentially received by the eight or less ultrasonic elements.

2. The ultrasonic thickness measurement device according to claim 1, wherein
    the ultrasonic probe further includes a base member configured to mount on the body, and
    the eight or less ultrasonic elements are at the base member.

3. The ultrasonic thickness measurement device according to claim 2, wherein the controller is further configured to:
    access a learning model including a parameter to acquire, from the tomographic image data, attribute information corresponding to the thickness of the target body tissue; and
    determine the attribute information corresponding to the thickness by using the learning model with, as input image data, the tomographic image data of the body of the subject; and
    determine the thickness from the determined attribute information.

4. The ultrasonic thickness measurement device according to claim 3, wherein
    with, as one set of data, the tomographic image data based on each of the received signals that is received from the target body tissue by the eight or less ultrasonic elements, and supervised image data corresponding to the tomographic image data and in a state where the thickness is determined,
    the learning model performs learning on a plurality of sets of data to set the parameter to acquire, from the tomographic image data, the attribute information corresponding to the thickness of the target body tissue.

5. The ultrasonic thickness measurement device according to claim 4, wherein
    the controller is coupled to the learning model via a communication unit in one of a wireless or wired manner, and
    the learning model is configured to have the parameter updated by new tomographic image data, and supervised image data corresponding to the new tomographic image data.

6. The ultrasonic thickness measurement device according to claim 3, wherein
    the controller is coupled to the learning model via a communication unit in one of a wireless or wired manner, and
    the learning model is configured to have the parameter updated by new tomographic image data, and supervised image data corresponding to the new tomographic image data.

7. The ultrasonic thickness measurement device according to claim 1, wherein the controller is further configured to:
    access a learning model including a parameter to acquire, from the tomographic image data, attribute information corresponding to the thickness of the target body tissue;
    determine the attribute information corresponding to the thickness by using the learning model with, as input image data, the tomographic image data of the body of the subject; and
    determine the thickness from the determined attribute information.

8. The ultrasonic thickness measurement device according to claim 7, wherein
    with, as one set of data, the tomographic image data based on each of the received signals that is received from the target body tissue by the eight or less ultrasonic elements, and supervised image data corresponding to the tomographic image data and in a state where the thickness is determined,
    the learning model is configured to perform learning on a plurality of sets of data to set the parameter to acquire, from the tomographic image data, the attribute information corresponding to the thickness of the target body tissue.

9. The ultrasonic thickness measurement device according to claim 8, wherein the controller is coupled to the learning model via a communication unit in one of a wireless or wired manner, and the learning model is configured to have the parameter updated by new tomographic image data, and supervised image data corresponding to the new tomographic image data.

10. The ultrasonic thickness measurement device according to claim 7, wherein the controller is coupled to the learning model via a communication unit in one of a wireless or wired manner, and the learning model is configured to have the parameter updated by new tomographic image data, and supervised image data corresponding to the new tomographic image data.

11. An ultrasonic thickness measurement method comprising determining a thickness of a target body tissue from tomographic image data of a body of a subject, wherein the tomographic image data is acquired by receiving, by receiving elements, a reflected wave of ultrasonic waves emitted to the body from eight or less ultrasonic elements each including a transmission element and a receiving element, the transmission element and the receiving element are the eight or less ultrasonic elements, the tomographic image data is based on received signals that are received by the eight or less ultrasonic elements, the tomographic image data is image data in which data of each of tomographic images of eight or less lines corresponding to the eight or less ultrasonic elements is arranged, along a depth direction from a skin surface of the body of the subject, the thickness is determined from the tomographic image data that is acquired by arranging, in association with an arrangement of each of the eight or less ultrasonic elements, B-mode images generated from A-mode images, and the A-mode images are generated by processing each of the received signals that is sequentially received by the eight or less ultrasonic elements.

12. The ultrasonic thickness measurement method according to claim 11 comprising:

accessing a learning model including a parameter for acquiring, from the tomographic image data, attribute information corresponding to the thickness of the target body tissue;

determining the attribute information corresponding to the thickness by using the learning model with, as input image data, the tomographic image data of the body of the subject; and determining the thickness from the determined attribute information.

\* \* \* \* \*